(12) United States Patent
Lauritsch et al.

(10) Patent No.: US 8,285,014 B2
(45) Date of Patent: Oct. 9, 2012

(54) MEASURING BLOOD VOLUME WITH C-ARM COMPUTED TOMOGRAPHY

(75) Inventors: Guenter Lauritsch, Erlangen (DE); Thomas Redel, Poxdorf (DE); Michael Zellerhoff, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 1180 days.

(21) Appl. No.: 12/061,357

(22) Filed: Apr. 2, 2008

(65) Prior Publication Data
US 2008/0247503 A1 Oct. 9, 2008

Related U.S. Application Data

(60) Provisional application No. 60/910,504, filed on Apr. 6, 2007.

(51) Int. Cl.
*G06K 9/00* (2006.01)
*H05G 1/64* (2006.01)

(52) U.S. Cl. ......... 382/128; 382/131; 378/4; 378/98.11; 378/98.12

(58) Field of Classification Search .................. 382/128; 378/8, 98.11, 98.12
See application file for complete search history.

(56) References Cited

U.S. PATENT DOCUMENTS

| | | | | |
|---|---|---|---|---|
| 4,835,688 | A * | 5/1989 | Kimura | 345/424 |
| 5,412,562 | A | 5/1995 | Nambu et al. | |
| 5,647,360 | A * | 7/1997 | Bani-Hashemi et al. | 600/425 |
| 6,154,518 | A * | 11/2000 | Gupta | 378/62 |
| 6,196,715 | B1 * | 3/2001 | Nambu et al. | 378/197 |
| 6,373,920 | B1 * | 4/2002 | Hsieh | 378/98.11 |
| 2002/0191735 | A1 * | 12/2002 | Strobel | 378/4 |
| 2005/0046644 | A1 * | 3/2005 | Ohishi | 345/643 |
| 2006/0082598 | A1 * | 4/2006 | Ohishi et al. | 345/653 |
| 2006/0171578 | A1 * | 8/2006 | Novak | 382/131 |
| 2007/0104317 | A1 * | 5/2007 | Ohishi | 378/98.12 |
| 2007/0140537 | A1 * | 6/2007 | Heigl et al. | 382/128 |
| 2007/0165917 | A1 * | 7/2007 | Cao et al. | 382/128 |
| 2008/0008367 | A1 * | 1/2008 | Franaszek et al. | 382/128 |

FOREIGN PATENT DOCUMENTS

JP 2004159983 A 6/2004

OTHER PUBLICATIONS

Eastwood et al., Perfusion CT with Iodinated Contrast Material, America Roentgen Ray, AJR:180, 2003, pp. 3-12.*

(Continued)

*Primary Examiner* — Alexander H Taningco
(74) *Attorney, Agent, or Firm* — Lempia Summerfield Katz LLC

(57) ABSTRACT

A system and method of obtaining perfusion data for cerebral tissue is described. The system includes a C-arm X-ray device and a computing system configured to obtain sets of rotational projection X-ray data suitable for reconstructing 3D voxel data sets. A first data set is obtained of the patient, and then contrast material is injected into the vascular system to obtain a second 1 data set. A first voxel data set is subtracted from the second voxel data set, and the resultant data set is processed so as to segment the contrast-enhanced vasculature from the remaining data. The segmented voxels are subtracted from the resultant voxel data set, so as to yield a functional data set representing the difference between the attenuation of the tissues after administering contrast agent and the tissues prior to administering the contrast agent, without the contrast enhanced vasculature. The attenuation of the functional data set represents the perfusion or cerebral blood volume (CBV).

19 Claims, 6 Drawing Sheets

OTHER PUBLICATIONS

Adam et al., Absolute Cerebral Blood Volume and Bood Flow Measurements Based on Synchrontron Radiation Quantative Computed Tomography, Journal of Cerebral Blood Flow & Metabolism, 2003, pp. 499-512.*

Fahrig, R., et al., "Dose and image quality for a cone-beam C-arm CT system," Med. Phys. 33 (12), Dec. 2006, © 2006 Am. Assoc. Phys. Med., pp. 4541-4550.

Hamberg, L., et al., "Measurement of Cerebral Blood Volume with Subtraction Three-dimensional Functional CT," AJNR Am J Neuroradiol, Nov. 1996, pp. 1861-1869.

Hunter, G., et al., "Whole-Brain CT Perfusion Measurement of Perfused Cerebral Blood Volume in Acute Ischemic Stroke: Probability Curve for Regional Infarction," Radiology, Jun. 2003, pp. 725-730.

Sa de Camargo, E., et al., "Neuroimaging of Ischemia and Infarction," vol. 2, 265-276, Apr. 2005, © The American Society for Experimental NeuroTherapeutics, Inc., pp. 265-276.

Schramm, P., et al., "Comparison of Perfusion Computed Tomography and Computed Tomography Angiography Source Images With Perfusion-Weighted Image and Diffusion-Weighted Imaging in Patients With Acute Stroke of Less Than 6 Hours' Duration," *Stroke*, Copyright © 2004 American Heart Association, originally published online May 20, 2004, located on the World Wide Web at: http://stroke.ahajournals.org/cgi/content/full/35/7/1652, 9 pages.

Tomandl, B., et al., "Comprehensive Imaging of Ischemic Stroke with Multisection CT[1]," Radiographics, © RSNA, 2003, located on the World Wide Web at: http://radiographics.rsnajnls.org/cgi/content/full/23/3/565?maxtoshow, 53 pages.

Wintermark, M., et al., "Perfusion-CT Assessment of Infarct Core and Penumbra: Receiver Operating Characteristic Curve Analysis in 130 Patients Suspected of Acute Hemispheric Stroke," *Stroke*, Copyright © 2006 American Heart Association, originally published online Mar. 2, 2006, located on the World Wide Web at: http://stroke.ahajournals.org/cgi/content/full/37/4/979, 8 pages.

\* cited by examiner

MEASURING BLOOD VOLUME WITH C-ARM COMPUTED TOMOGRAPHY

The present application claims the benefit of priority to U.S. Provisional Application Ser. No. 60/910,504, which was filed on Apr. 6, 2007 and which is incorporated herein in its entirety by reference.

TECHNICAL FIELD

This application relates to a system and method for measuring blood volume in a patient.

BACKGROUND

Several imaging modalities are available for use imaging in the diagnosis of cerebral conditions such as stroke, AVM (arteriovenous malformation), or cancer. Imaging modalities include CT (computed tomography) and MRI (magnetic resonance imaging), and are able to obtain anatomical and physiological information about an organ such as the brain.

Perfusion, which is the circulation of blood through tissue, is one indicator used for diagnosing a region of interest in a patient affected by a vascular stenosis or blockage. By determining perfusion at the capillary level of the region of interest, the effect of the stenosis or blockage of an artery can be assessed and localized directly. The extent of the stenosis or blockage can also be determined. From this information, a therapeutic treatment can be planned, and its success can then be monitored after the intervention by subsequently re-determining the perfusion of the region of interest.

When using CT, for example, images may be obtained to that provide functional information. Non-enhanced CT (NECT, which may also be called non-contrast CT, NCCT) as well with contrast enhanced CT angiography (CTA) with conventional contrast agents may be used for initial diagnosis. The administered contrast agent may also be used to visualize and measure perfusion of the organ. Parameters which may be considered include, for example, perfusion (F), blood volume (CBV), mean transit time (MTT), time to peak (TTP). Important diagnostic information can also be derived from a comparison of the various variables with one another to ascertain inconsistencies.

CT imaging methods are generally used pre-interventionally; that is, during the diagnostic phase in an emergency room. But, CT and MRI equipment is generally not available in the angiography laboratory where interventional therapy is performed. However, a typical hospital interventional laboratory may have a C-arm-based X-ray system. Thus, at present, the functional evaluation of a patient during the interventional phase is done qualitatively using 2D projection images.

Clinical studies have shown that there is a significant correlation between, for example cerebral blood volume (CBV) and the prognosis for a patient with acute stroke. Recent studies indicate that severely reduced cerebral blood volume is an important predictor for essentially non-viable tissue, and that CBV-determined lesion volumes are significantly correlated with follow-up lesion volumes as measured using CT.

A procedure for measuring CBV includes the obtaining a CT or MRI imaging data set of the brain before and after the intravenous administration of contrast agent. The difference between the two data sets corresponds to the contrast agent present in the brain and can thus be converted into the blood volume.

The tissue blood volume may be determined by subtracting the measured density of tissue, measured in Hounsfield units (HU) for the data sets with and without contrast agent. The image density in HU is linearly proportional to the concentration of the contrast agent in the blood and brain tissue. This change in contrast agent may be interpreted as blood volume as the blood-brain barrier prevents the contrast agent from escaping the circulatory system, and the change in density may thus be interpreted as being localized to the vasculature.

Absolute values of the CBV may be computed on a global or local basis, or qualitative comparisons of bilateral CBV so as to identify volumes having impaired circulation.

When this procedure is performed diagnostically, the contrast agent is injected intravenously, rather than arterially. The level of contrast agent needs to be kept constant during the image data set acquisition so that normalized measurements can be obtained. This involves a complex injection protocol and a relatively high amount of contrast agent. Moreover, the contrast differences between vessels and bones in intravenous contrast agent injection are very slight, which leads to difficulties in reconstructing the larger vessels in a perfused area in the head or in the region of the base of the skull. However, increasing the amount of contrast agent is contraindicated by an association with poorer outcomes.

SUMMARY

A system and method for measuring cerebral blood volume (CBV) is described. The system may be in an interventional radiology laboratory and may be used for both diagnosis and treatment of a patient with a suspected ischemic stroke.

In an aspect, a system for obtaining perfusion images includes a C-arm X-ray device; a computer operative to accept a plurality of projection X-ray images representing a first data set of a patient, and a second data set of images of a patient, and to convert each of the first and second data sets to volumetric data sets. The second data set is contrast enhanced data, and a cerebral blood volume (CBV) is computed from the first and the second volumetric data sets (voxels). The patient may remain positioned on a patient support table during the process of obtaining the first and second data sets. The patient may remain in position for therapy.

A method of computing cerebral perfusion of a patient including obtaining a first computed tomographic (CT)-like data set and processing the data so that a first voxel data set is produced; administering a contrast agent and obtaining a second CT-like data set. This second data set is a CT angiographic data set (CTA). The second CT-like data set is processed so as to result in a second voxel data set (three-dimensional CTA). The first voxel data set may be subtracted from the second voxel data set to yield a third voxel data set, which is a three dimensional digitally subtracted angiogram (DSA) without the background tissue and any bone which may be present in the field of view. Further steps of the method include segmenting the third voxel set so as to obtain a fourth voxel data set representing contrast-enhanced vasculature; excising the fourth voxel data from the third voxel data set to form a fifth voxel data set. The attenuation of each voxel of the fifth voxel data set may be interpreted as representing the perfusion of the parenchyma. This may also be presented as a cerebral blood volume (CBV).

In an aspect, the method may alternatively include processing the fourth voxel data set to form a plurality of 2-dimensional projection radiographic images of the segmented vasculature of the DSA for use as mask images; subtracting the mask projection images from the 2-dimensional radiographic images of the second (contrast enhanced) CT-like data set to form a plurality of masked projection images; optionally, interpolating each of the masked projection images within the boundary of the masked portion of an image; and, reconstructing a new CTA voxel data set, having the contrast enhanced vasculature excised, from the interpolated masked projection images. The first voxel data set (representing the non-contrast enhanced first CT-like data set) may be subtracted from the new CTA voxel data set to form a DSA voxel data set with the vasculature excised therefrom, so as to form a fifth voxel data set as above.

A computer program product is described, the product being stored or distributed on a computer readable medium. The product includes instructions executable on a computer so as to configure the computer to perform the operations of: obtain a first computed tomographic (CT)-like data set and processing the data so that a first voxel data set is produced; obtain a second CT-like data set where the patient has been administered a contrast agent; and, to segment a second voxel data set obtained from the second CT-like data set so as to obtain a third voxel data set of contrast-enhanced vasculature. Further, the computer is configured to excise the data set of the contrast enhanced vasculature from the second voxel data set to form a fourth voxel data set. The first voxel data set may be subtracted from the fourth voxel data set to form a fifth voxel data set.

DESCRIPTION

Figure 1:
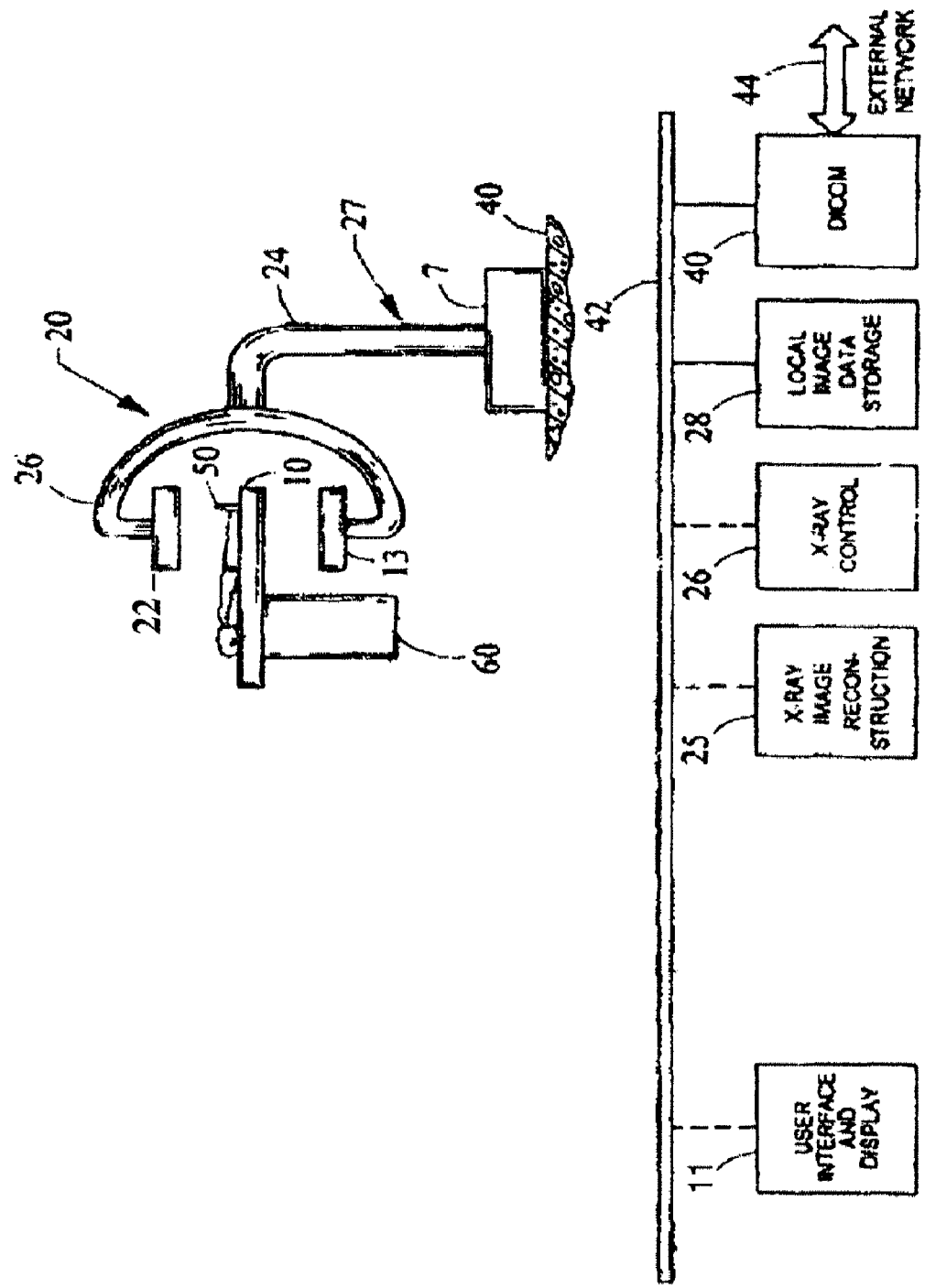
FIG. 1 is a block diagram of a C-arm X-ray device, with data processing and control equipment for acquiring and processing CT-like image data of a patient.

Reference will now be made in detail to embodiments. While the invention will be described in conjunction with these embodiments, it will be understood that it is not intended to limit the invention to such embodiments. In the following description, numerous specific details are set forth in order to provide a thorough understanding of the present invention which, however, may be practiced without some or all of these specific details. In other instances, well known process operations have not been described in detail in order not to unnecessarily obscure the description.

The embodiments described herein include methods, processes, apparatuses, instructions, or systems for diagnosing patients presenting with one or more symptoms which may be indicative of a stroke. However, the examples of diseases, syndromes, conditions, and the like, and the types of examination, diagnosis and treatment protocols described herein are by way of example, and are not meant to suggest that the method and system is limited to those named, or the equivalents thereof. As the medical arts are continually advancing, the use of the methods and system described herein may be expected to encompass a broader scope in the diagnosis and treatment of patients.

The combination of hardware and software to accomplish the tasks described herein is termed a system. Where otherwise not specifically defined, acronyms are given their ordinary meaning in the art.

The instructions for implementing processes or methods of the system, may be provided on computer-readable storage media or memories, such as a cache, buffer, RAM, FLASH, removable media, hard drive or other computer readable storage media. Computer readable storage media include various types of volatile and nonvolatile storage media. The functions, acts or tasks illustrated in the figures or described herein may be executed in response to one or more sets of instructions stored in or on computer readable storage media. The functions, acts or tasks may be independent of the particular type of instruction set, storage media, processor or processing strategy and may be performed by software, hardware, integrated circuits, firmware, micro code and the like, operating alone or in combination. Likewise, processing strategies may include multiprocessing, multitasking, parallel processing and the like.

In an embodiment, the instructions may be stored on a removable media device for reading by local or remote systems. In other embodiments, the instructions may be stored in a remote location for transfer through a computer network, a local or wide area network or over telephone lines. In yet other embodiments, the instructions are stored within a given computer or system.

The instructions may be a computer program product, stored or distributed on computer readable media, containing some or all of the instructions to be executed on a computer to perform all or a portion of the method or the operation of the system.

An X-ray imaging modality may comprise an X-ray tube, high-voltage power supply, radiation aperture, X-ray detector, digital imaging system, system controller, as well as user control and display units. The X-ray detectors may be amorphous Silicon (a-Si), amorphous Selenium (a-Se), PbI2, CdTe or HgI2 detectors using direct detection and TFT technology, or indirect detectors as is known in the art, or may be subsequently be developed, to provide high resolution, high-dynamic-range real-time X-ray detection. The X-ray detector may be disposed diametrically opposed to the X-ray source and such that the plane of the detector is substantially perpendicular to the axis of the X-ray source. This orientation may, for example, be maintained by attaching the X-ray source and X-ray detector to a C-arm, a U-arm or the like. The C-arm may be mounted to a robot so as to permit the X-ray source and detector to be oriented with respect to the patient.

The C-arm X-ray device is provided with an X-ray source and an X-ray detector, and may be operated to obtain fluoroscopic images, data suitable for the production of 2D radiographic images, or computed tomography (CT)-like slices or 3D images.

The use of the term CT-like data or CT-like images is understood to encompass data and images obtained by a CT X-ray device or other tomographic imager. FIG. 1 shows a block diagram of an example of a system for the diagnosis and treatment of an illness of a patient. Other embodiments of the system may include more than, or fewer than all of the devices, or functions, shown in FIG. 1.

The data processing and system control is shown as an example, and many other physical and logical arrangements of components such as computers, signal processors, memories, displays and user interfaces are equally possible to perform the same or similar functions. The particular arrangement shown is convenient for explaining the functionality of the system.

The C-arm X-ray device 20 may comprise a C-arm support 26 to which an X-ray source 22, which may include a diaphragm to limit the field of view, and an X-ray detector 13 may be mounted so as to face each other about an axis of rotation. The C-arm 26 may be mounted to a robotic device 27 comprising a mounting device 7, and one or more arms 24 which are articulated so as to be capable of positioning the C-arm X-ray device with respect to a patient support apparatus 10. The robotic device 27 may be controlled by a control unit 26, which may send commands causing a motive device (not shown) to move the C-arm 24. The motive device may be a motor or a hydraulic mechanism. The mounting device may be mounted to a floor 40 as shown, to a ceiling or to a wall, and may be capable of moving in longitudinal and transverse directions with respect to the mounting surface.

The C-arm X-ray device 20 is rotatable such that a sequence of projection X-ray images may be obtained by an X-ray detector 13 positioned on an opposite side of the patient from the X-ray source 22, and the images may be reconstructed or re-projected by any technique of processing for realizing computed tomographic (CT)-like, 2-D, real-time fluoroscopic images, or 3D voxel data sets and CT-like sectional views. A patient 50 may be positioned on a patient support apparatus 10. The patient support apparatus 10 may be a stretcher, gurney or the like and may be attached to a robot 60. The patient support apparatus 10 may also be attached to a fixed support or adapted to be removably attached to the robot. Aspects of the patient support apparatus 10 may be manipulable by the robot 60. Additional, different, or fewer components may be provided.

The C-arm X-ray radiographic device 20 and the associated image processing 25 may produce angiographic and computed tomographic images comparable to, for example, CT equipment, while permitting more convenient access to the patient for ancillary equipment and treatment procedures. The properties of the X-ray detector used in a C-arm X-ray device may result in the computation of smaller voxel volumes.

A separate processor 25 may be provided for image processing, or the function may be combined with other processing functions. The various devices may communicate with a DICOM (Digital Communications in Medicine) system 40 and with external devices over a network interface 44, so as to store and retrieve image and other patient data.

Images reconstructed from the X-ray data may be stored in a non-volatile (persistent) storage device 28 for further use. The X-ray device 20 and the image processing attendant thereto may be controlled by a controller 26 or the function may be consolidated with the user interface and display 11.

The X-ray images may be obtained with or without various contrast agents that are appropriate to the imaging technology and diagnosis protocol being used.

Apart from the sensors and positioning capabilities, the imaging, data processing, and controlling equipment may be located within the treatment room or remotely, and the remotely-located equipment may be connected to the treatment room by a telecommunications network. Aspects of the diagnosis and treatment may be performed without personnel, except for the patient, being present in any of the local treatment rooms.

The X-ray imaging device may be operated to obtain CT-like data by rotating the C-arm such that the opposed X-ray source and X-ray detector traverse an angular range of at least about 180 degrees about an axis perpendicular to the principal axis of radiation of the C-arm during a short time period (for example 5 or 10 seconds). A 3D image may be reconstructed from the detected X-ray data, or 2D images or fluoroscopic images may be reconstructed in various image planes. The algorithmic and measurement aspects of computed tomography images are being improved, and the processing of the images obtained by the imaging devices are expected to continue to improve in resolution and dynamic range, speed, and in reduction of the X-ray dosage.

In an example, a method of diagnosing and treating a patient may include the steps of: obtaining a NECT C-arm CT data set, and storing the image data in a memory device. This image data set may be obtained either before catheter introduction (non-invasively) or after catheter introduction (minimally invasive), so as to produce an image set for a first diagnosis in a patient presenting with symptoms which may indicate a stroke. Where the stroke is determined to be ischemic, rather than hemorrhagic, or another syndrome, another C-arm CT data set may be obtained with an administered contrast agent. Such a data set may be designated as a CTA data set (CT angiography). This is done by administering a contrast agent by programmed injection such that, during the period of time where the CTA data set is obtained, the density of contrast agent is maintained substantially constant.

After stabilization of the contrast density, a contrast enhanced C-arm CT data set may be obtained (e.g., the CTA). The duration of the injection should be long enough such that the parenchyma (e.g., neuron tissue of the brain) is substantially saturated.

After the CTA data set is obtained, the data NECT and the CTA data sets may be reconstructed into 3D CT voxel data sets by techniques which are now well known. Of course, both the mathematical, algorithmic and computational aspects of this reconstruction are the subject of continuing research and development, and the specific method that is to be used is chosen so as to take advantage of these evolutions.

The result of the 3D reconstructions are data sets of voxels representing the attenuation value associated with a plurality of individual small volumes (voxels) of the volume that has been imaged. It may be necessary re-register the relative coordinate systems of the data sets (such as the NECT and CTA voxel data sets) to account for any patient movement that has occurred during the previous steps of the method. Such movement of the patient may occur between the recording of the NECT and the CTA data sets where the NECT data set is first used to exclude a cerebral hemorrhage, and a port, for example for arterial access, may then be put in place for further diagnosis and treatment. Image re-registration techniques may adjust the relative coordinate systems so as to minimize the differences between salient points of the data sets, but any technique that achieves the same effective result may be used.

The two sets of data, that is, the NECT and the CTA voxel data sets, may be subtracted from each other so as to produce a data set of the contrast enhancement of the plurality of voxels due to the contrast agent as representative of blood. This process may be termed digital subtraction angiography (DSA), and here the process is performed volumetrically. Segmentation of the CTA data set may also be performed so as to permit the larger blood vessels in the data set to be subtracted (excised) from the data set. This may also be done, for example, by establishing a threshold value in HU and excluding the data exceeding the threshold value. The voxel data obtained by subtraction of the NECT voxel data from the CTA voxel data may be termed a functional CT image as the contrast difference (enhancement) is attributed to the contrast agent and representative of the cerebral perfusion. This permits the computation of CBV. The segmentation of the vasculature and excision from the voxel data set may remove both large vessels and smaller vessels, so that the high-contrast of the contrast-enhanced vessels has a smaller error contribution to a CBV calculation, which may be made on a voxel-by-voxel basis. The voxels where contrast-enhanced segmented vascular structures have been excised from the data set may be either used directly, or the data may be locally smoothed by interpolation.

The CTA data may also be used to identify and characterize other aspects of the circulation such as displaying the vessels and evaluating the blocked regions or stenoses.

Once the data set has been processed in this manner, the expert may then proceed with the evaluation of the patient, including the visualization of the cerebral blood volume. This may be done using slice representations in an appropriate viewing plane, by false color images, by maximum intensity projections (MIP), or the like.

The number of projection images obtained with contrast agent injection using rotation of the C-arm may be limited due to operational considerations such as arm rotation speed, duration of the procedure, and the like. When only a limited number of images is used to reconstruct the volumetric attenuation values, high contrast regions such as vessels with contrast agent may cause streak artifacts in the reconstructed data set and projection images thereof. Such artifacts may result in mis-estimation of the local CBV, as the artifacts may not be representative of the actual voxel density. This phenomenon may be mitigated by additional data processing steps.

After reconstructing the volumetric data sets as described above, and performing a volumetric DSA the blood vessels of the volumetric DSA data set may be segmented. The segmented vessels may then be processed so as to form projected radiographs of the segmented blood vessels onto image planes corresponding to image planes of the projection images (digitally reconstructed radiographs (DRR)) corresponding to the projection images of the CTA data set. As such, the re-projected segmented vasculature may be used as a mask to excise the blood vessels from the CTA projection images. After the high-opacity blood vessels have been subtracted or excised from the projection images of the functional data set, the modified projection images of the CTA data set may be interpolated over the areas where the blood vessels have been excised from the image, so as to reduce density discontinuities.

The resultant data set, having the blood vessels excised, and the gaps interpolated, may now be used as a set of projection images so as to reconstruct the projection image data set to a volumetric data set. In this manner, effects of the blocked vessels and any artifacts associated therewith are either eliminated or mitigated, facilitating the use of the voxel data set, and images produced therefrom. The NECT voxel data set may then be subtracted from the CTA data set from which the contrast-enhanced vessels have been excised, so as to form a functional data set for visualizing or computing CBV.

It is possible also to re-superimpose the segmented blood vessels on the voxel functional data set. The blood vessels may be differentiated by color or other means from the neurons when images are be produced for diagnostic evaluation, or as part of a therapeutic protocol.

Where the contrast-enhanced vessels have been segmented, the blood vessels may be displayed with a better representation, such as a higher contrast, and better visual identification of the blood vessels, even small vessels, is possible. The influence of the smaller vessels may be better taken into account in the computation of CBV when quantitative data is being obtained.

While the technique for determining blood volume has been described with particular reference to the brain, it should be understood that the system and method can be used with respect to other organs and body parts, and the reduction of artifacts arising from high contrast differences may likewise be mitigated.

Figure 2:
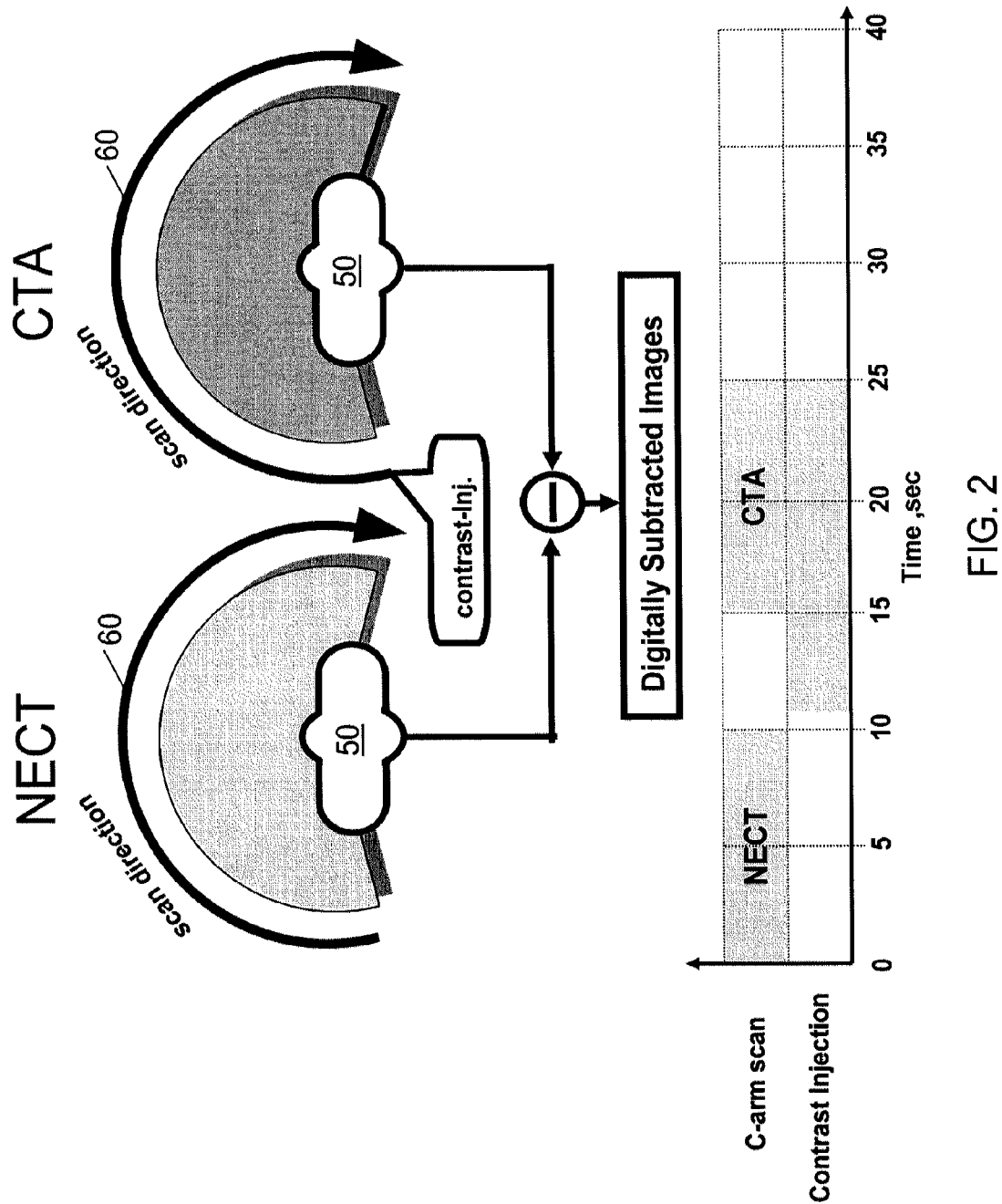
FIG. 2 is a schematic representation of the data-taking operations for obtaining a non-contrast-enhanced CT (NECT) and a contrast-enhanced CT (CTA), showing the time sequence of X-ray data acquisition and contrast agent injection.

In an example, of the use of the system of FIG. 1 in performing the methods described, FIG. 2 schematically indicates the temporal relationship between the data set acquisition and the administration of a contrast agent. The operation of the apparatus is shown at the top of the figure, where the patient 50 is shown with respect to the scanning direction 60 of the C-arm system 20 of FIG. 1. At the beginning of the protocol, the NECT data set is obtained by rotating the C-arm about the patient 50 during the first 10 seconds. Then, contrast agent is administered. There is an initial period of time, in this example 5 seconds, where the injected bolus is allowed to perfuse the region of interest and reach a suitable density, after which the rate of injection may be varied (typically slowed) so as to maintain a steady-state density for the period of acquisition of the CTA image data set.

In this example, the C-arm is again rotated during the period from 15 to 25 seconds after the commencement of the procedure, to obtain the CTA data set. Injection of contrast material may be varied during the rotation of the C-arm, so as to manage the temporal change in contrast agent density. While the time periods are shown with 5 second granularity, this is for convenience in explanation and other time durations for each of the steps and the relationships between them may be used. The CTA data set may not be obtained immediately after the NECT data set, as shown, as it may be necessary to inspect the NECT data, either as projection images or as a voxel data set, so as to exclude, for example, a hemorrhagic stroke, for which the administration of a contrast agent may not be appropriate. Other medical procedures such as installation of a port may also be performed between the acquisition of the NECT and CTA data sets.

The NECT and the CTA voxel data sets may volumetrically subtracted 70 to yield a DSA voxel data set 80. Alternatively, the corresponding projection images of the NECT and CTA data sets may be subtracted so as to create a projection DSA.

Figure 3:
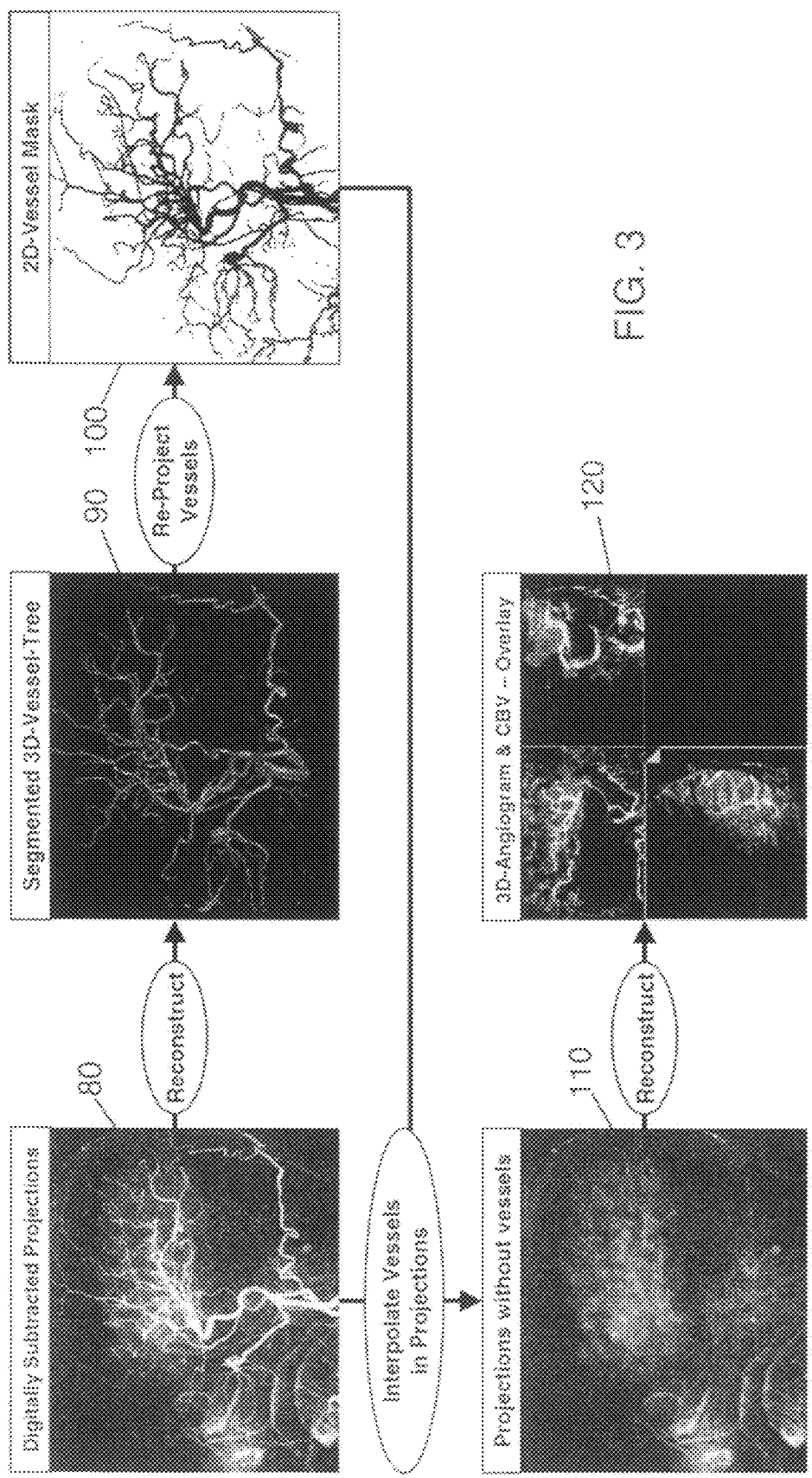
FIG. 3 shows a plurality of images representing the CT data during steps in an example of the process of excising the contrast-enhanced vasculature from the CTA voxel data set.

FIG. 3 shows the use of the projection radiographs 80 so as to excise the blood vessels from the functional data set. The projections 80 are used to reconstruct a voxel (3D) data set (not shown) from which blood vessels are segmented 90. The lumen of the blood vessel is observable, and defines the boundary between the blood vessel and other tissue. The segmented blood vessels may then be projected as projection images corresponding to the individual projection images of the CTA data set. One of the projected segmented contrast-enhanced blood vessel images is shown 100, where the image is thresholded so as to form a mask corresponding to the position of the blood vessels in the projection image. This mask may be used to excise the regions of the projection image of the subtracted NECT and CTA data. The excised regions may be interpolated so as to minimize density discontinuities, and a projection image without the contrast-enhanced vessels 110 may be produced. This may be useful for viewing the perfused regions of the brain. The set of projection images obtained by this process may be reconstructed so as to obtain a voxel (3D) data set representing the perfused regions. This data set may be then be used to produce 3D and slice images 120 of the brain, so as to use gray scale or false color techniques to qualitatively assess the CBV. This may be done on the basis of a left-to-right comparison, on a quantitative basis as a percentage with respect to a corresponding opposite parietal volume vale, or as an absolute value.

Figures 4A, 4B, 4C:
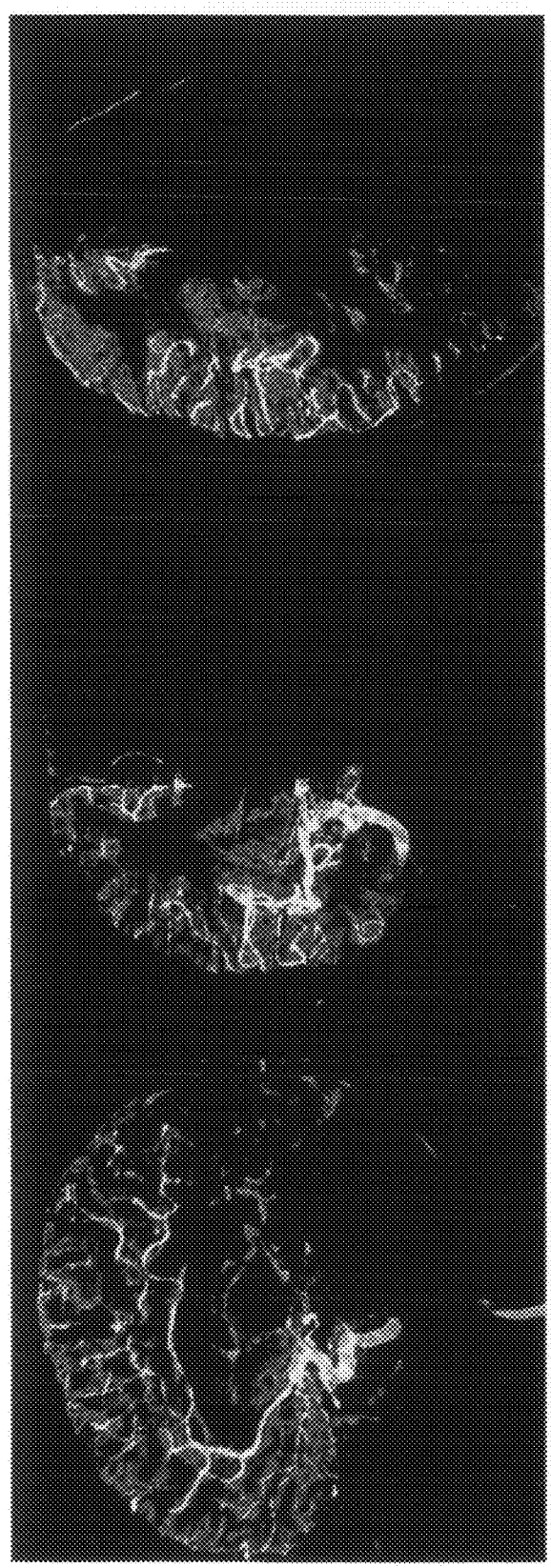
FIG. 4 A, B, C show three false-color images produced as orthogonal views of the functional voxel set, where the previously-excised contrast-enhanced vasculature voxel data set has been superimposed on the functional data set obtained by the process of FIG. 3.

The result of using the method on a patient may be seen in FIG. 4 where the sagittal, coronal, and transverse views of a patient are shown where the opacified blood vessels were segmented and subtracted from projection view, the projection views again reconstructed into a voxel data set of the perfusion information, and the segmented blood vessel data set used to generate image data of the blood vessels which were then superimposed of the appropriate CT view.

In an example of an intake protocol or method, a native (non enhanced CT, NECT) may be obtained to exclude hemorrhages, followed by rotational angiography (CTA) so as to display the contrast-enhanced blood vessels and evaluate the blocked vessels, and using the 3D functional image obtained by the methods described above so as to measure the CBV either qualitatively or quantitatively.

While the NECT image has been described as having been used to perform a preliminary diagnosis of the patient presenting with symptoms suggestive of a stroke, and make a diagnosis of an ischemic stroke, such a preliminary diagnosis may have been made using another imaging modality such as a spiral CT or MRI, or merely another C-arm CT that is available for use. The measurement of CBV and other aspects of the procedure described herein may then be subsequently performed.

Figure 5:
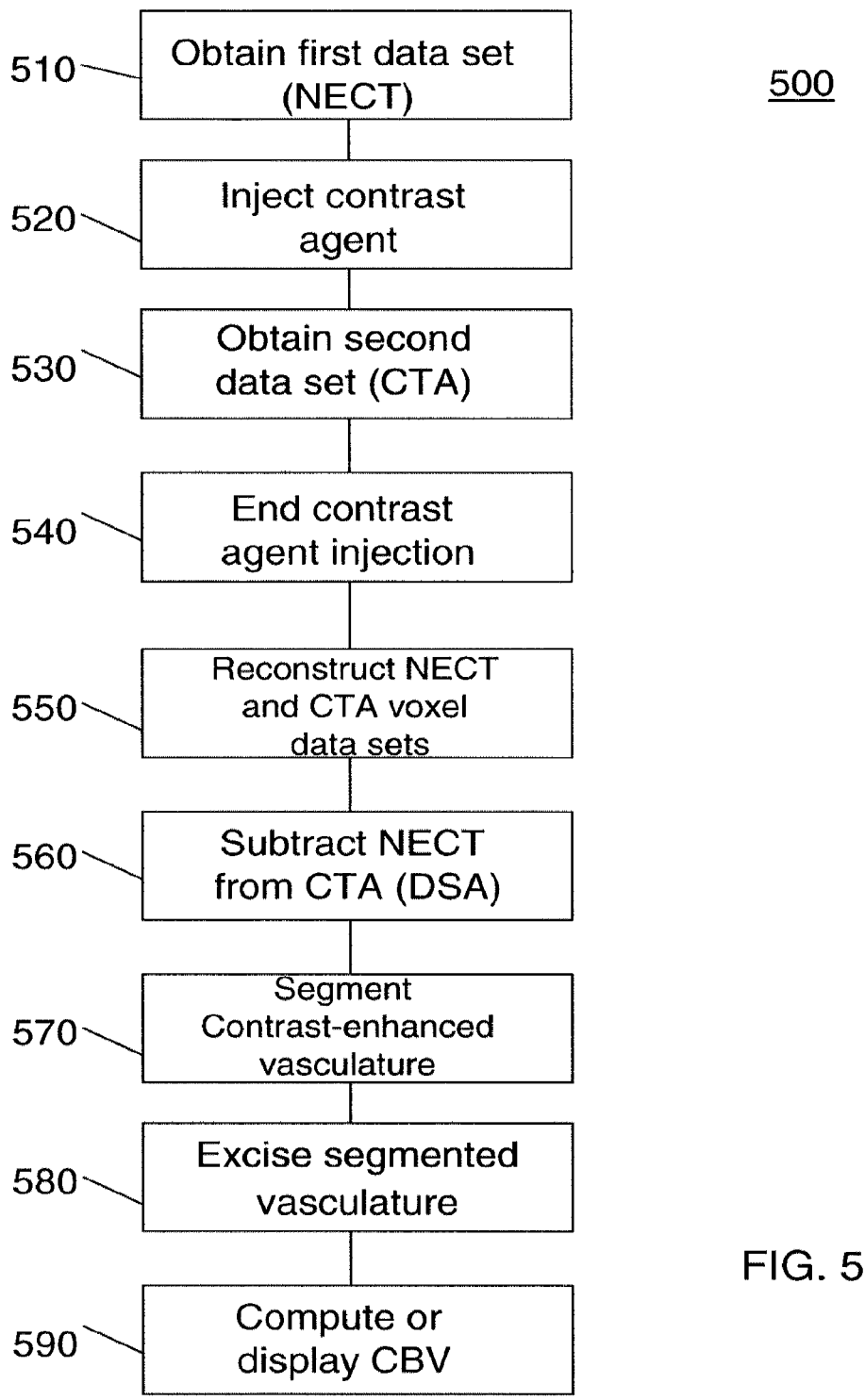
FIG. 5 is a flow diagram of the steps of the method of performing cerebral blood volume (CBV) analysis using functional CT data obtained from a C-arm X-ray device.

In an example shown in FIG. 5, the method 500 may include the steps of: moving the patient to the treatment room (not shown), and obtaining a sequence of C-arm X-ray rotational images suitable for reconstructing a first voxel data set of non-contrast enhanced (NECT) patient data (step 510). Providing that the indications from step 510 are interpreted so as to make the performance of a CT angiogram (CTA) an appropriate diagnostic or evaluation step, a contrast agent may be administered either venously or arterially (step 520) so as to establish a substantially constant level of enhancing agent in the perfused volume. A CTA is then performed (step 530) so as to obtain a second image data set for reconstructing a voxel data set representing the patient with the administered contrast agent. At about the time that the step of obtaining the CTA image data is completed, the administration of the contrast agent may be discontinued (step 540). The contrast agent may be administered intravenously or intra-arterially depending on the protocol. The NECT and CTA data sets are each reconstructed to form first and second voxel data sets, respectively (step 550). At this juncture, the coordinate frames first and second voxel data sets may be rotationally and translationally adjusted so as to compensate for any movement of the patient during the time interval between obtaining the two data sets. The first voxel data set (NECT) is subtracted from the second voxel data set (CTA) to form a digitally subtracted angiographic voxel data set (DSA) (step 560). The DSA data set may be processed so as to segment the contrast enhanced vasculature (step 570). The voxels that represent the volume occupied by the contrast-enhanced segmented vasculature are subtracted, voxel-by-voxel, from the DSA voxel data set (step 580), so as to minimize the amount of contrast-enhanced vasculature remaining in the second voxel data set. This results in a functional voxel data set that set represents the difference in contrast between the patient tissue and the contrast-enhanced patient tissue without the contrast enhanced vasculature, and this difference in contrast (attenuation) is interpretable as the voxel-by-voxel coronary blood volume (CBV). The functional voxel data set may be processed for display as any of the image types used in radiographic analysis or treatment (step 590) and the results may be stored as part of the patient records.

Since the patient may be on the treatment table when the CBV is performed, and treatment including stenting or thrombolysys performed, the method may be continued by returning to step 520, if needed, so as to obtain another set of second voxel data, and the remaining steps of the method performed so as to evaluate or document the results of the treatment.

In an aspect, the method as described above may be performed while the patient remains in the treatment room and on the support for the C-arm X-ray apparatus, so that both diagnosis, treatment, and follow up evaluation may be performed without moving the patient between diagnostic or treatment equipment suites. This may minimize the time between the diagnosis and treatment steps, which has been shown to have a beneficial effect on clinical outcomes.

In another aspect, the step of excising the contrast enhanced vasculature (step 570) may be modified when the high contrast of the vasculature results in artifacts in the reconstructed voxel set.

Figure 6:
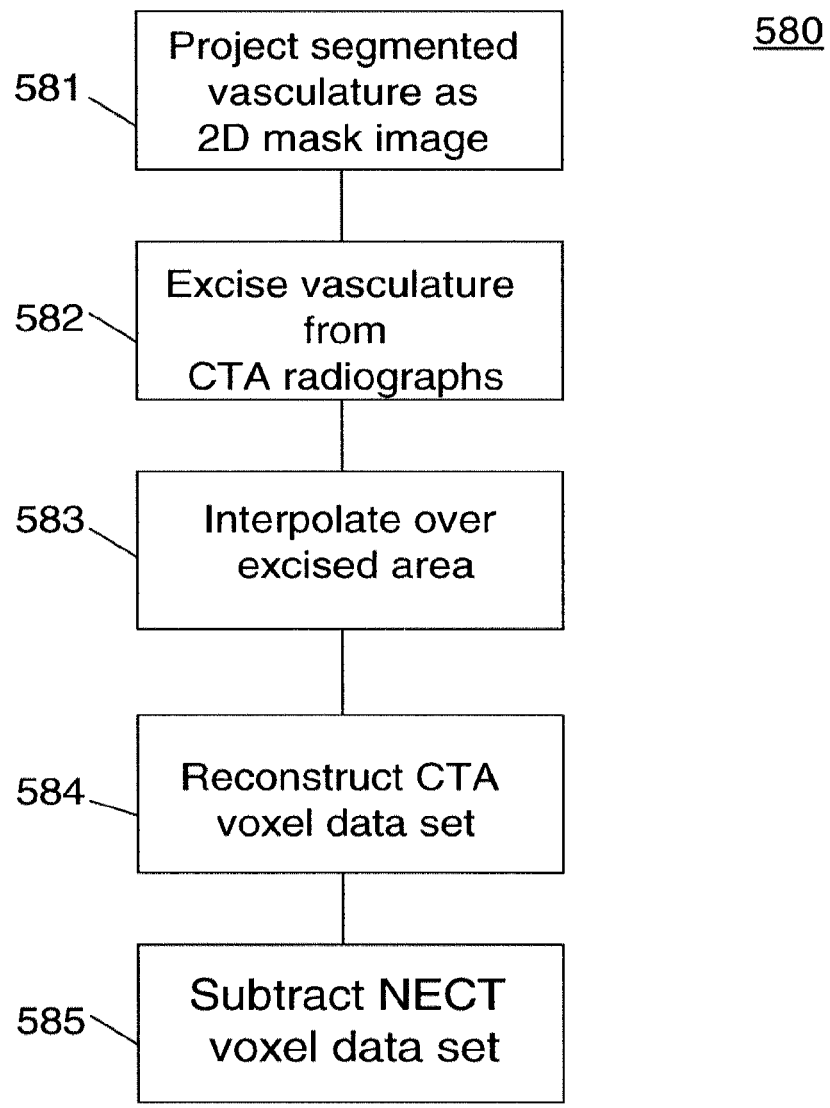
FIG. 6 is a flow diagram of a modification of the method of FIG. 5 to excise high-contrast structures from the contrast-enhanced voxel data set.

FIG. 6 shows an alternative data processing method for steps 580. The results of step 570, which is a voxel set representing the segmented contrast-enhanced vasculature is re-projected into a plurality of projection radiographs (step 581). The projection radiographs of step 561, being only of the contrast-enhanced vasculature, may be used as a mask to subtracted from the projection images obtained during the performance of step 530 (step 582). The data set may be interpolated (step 583) within the boundaries of the excised areas so as to reduce the contrast discontinuities in the data. Step 583 may be omitted. The projection data set resulting from step 582 (and, optionally, step 583) may be used to reconstruct a voxel data set (step 584) of CTA voxel data. This reconstructed voxel data set represents the tissue of the brain with the high-contrast vasculature and any associated artifacts removed. The NECT voxel data set, representing the non-contrast enhanced tissue may then be subtracted from the voxel data set resulting from step 584 so as to produce a new DSA (step 585). The process then proceeds to step 590.

The terms "subtracting" and "excising," when used in describing the processing of data sets herein is understood to mean either taking the difference between the values of the voxels on a linear or logarithmic basis, depending on the way in which the values are expressed, as is known in the art; or, alternatively, setting the value of a voxel corresponding to a segmented contrast-enhanced blood vessel or similar structure, to a fixed value. The value may be zero, or a value representing a mean density of the surrounding voxels, or the like.

The methods disclosed herein have been described and shown with reference to particular steps performed in a particular order; however, it will be understood that these steps may be combined, sub-divided, or reordered to from an equivalent method without departing from the teachings of the present invention. Accordingly, unless specifically indicated herein, the order and grouping of steps is not a limitation of the present invention. Also, where data sets are used in intermediate steps of the method, such data sets may be discarded, used only as computational conveniences and not stored, or combined with other data sets, without resulting in a different result from performing the method.

While the preferred embodiments of the invention have been described, it should be understood that the invention is not so limited and modifications may be made without departing from the invention. The scope of the invention is defined by the appended claims, and all systems and methods and products that come within the meaning of the claims, either literally or by equivalence, are intended to be embraced therein.

What is claimed is:

1. A system for obtaining perfusion images comprising:
a C-arm X-ray device; and
a computer operative to:
   accept a plurality of projection X-ray images representing a first data set of a patient and a second data set of a patient;
   convert each of the first data set and the second data set to form a first volumetric data set and a second volumetric data set, respectively;
   process the second volumetric data set to form a data set of segmented contrast-enhanced blood vessels;
   excise the segmented contrast-enhanced blood vessels from the second volumetric data set to form a third volumetric data set; and
   subtract the first volumetric data set from the third volumetric data set to form a fourth volumetric data set that represents a cerebral blood volume (CBV) on a voxel-by-voxel basis,
   wherein the second data set is contrast-enhanced data.

2. The system of claim 1, wherein the computation of the CBV is performed on a voxel-by-voxel basis.

3. The system of claim 1, wherein the computer is operative to process the data set of segmented contrast-enhanced blood vessels to form a set of projection radiographs corresponding to projection radiographs of the second data set.

4. The system of claim 3, wherein the computer is operative to subtract a plurality of projection images formed from the data set of segmented contrast-enhanced blood vessels from corresponding projection radiographs of the second data set.

5. The system of claim 4, wherein the computer is operative to:
   interpolate projection images resulting from the subtraction of the plurality of projection images from the corresponding projection radiographs between values at internal boundaries of the images corresponding to outer boundaries of the projected, segmented, contrast-enhanced blood vessels to form new projection images; and
   reconstruct the new projection images to form the third volumetric data set.

6. The system of claim 5, wherein the computer is operative to subtract the first volumetric data set from the third volumetric data set on a voxel-by-voxel basis to form a functional voxel data set.

7. The system of claim 6, wherein the functional voxel data set is used to compute the CBV.

8. The system of claim 5, wherein the third volumetric data set is used to compute a CT-slice, a 3D image, or a combination thereof.

9. The system of claim 8, wherein the CT-slice, the 3D image, or the CT-slice and the 3D images are displayed in false color, the false color being representative of the CBV of voxels of a functional voxel data set.

10. The system of claim 9, wherein the computer is operative to superimpose the segmented contrast-enhanced blood vessels on images produced from the functional data set.

11. A method of computing perfusion of a patient, the method comprising:
   obtaining a first computed tomographic (CT)-like data set and processing the first CT-like data set so that a first voxel data set is produced;
   administering a contrast agent;
   obtaining a second CT-like data set and processing the second CT-like data set so that a second voxel data set of contrast-enhanced data is produced;
   subtracting the first voxel data set from the second voxel data set to form a third voxel data set;
   segmenting the third voxel data set so as to obtain a fourth voxel data set representing contrast-enhanced vasculature;
   excising the fourth voxel data set from the third voxel data set to form a fifth voxel data set; and
   interpreting an attenuation of each voxel of the fifth voxel data set as representing a perfusion value of a parenchyma.

12. The method of claim 11, wherein administering the contrast agent includes vascularly administering the contrast agent and stabilizing a density of the contrast agent in a cerebral volume such that the density remains stable during a period of time when the second CT-like data set is obtained.

13. The method of claim 12, wherein the fifth voxel data set is processed to form CT-slice images.

14. The method of claim 13, wherein the fourth voxel data set is processed to overlay the segmented contrast-enhanced vasculature on at least some of the CT-slice images formed from the fifth voxel data set.

15. The method of claim 11, further comprising:
   processing the fourth voxel data set to form a first plurality of 2-dimensional radiographic mask images, and subtracting the first plurality of 2-dimensional radiographic mask images from a corresponding second plurality of 2-dimensional radiographic images obtained during the obtaining of the second CT-like data set to form a third plurality of 2-dimensional radiographic images;
   reconstructing a sixth voxel data set from the third plurality of 2-dimensional radiographic images; and
   subtracting the first voxel data set from a seventh voxel data set for computing the perfusion.

16. The method of claim 15, wherein each 2-dimensional radiographic image of the third plurality of 2-dimensional radiographic images is interpolated within a region where the segmented contrast-enhanced vasculature is subtracted.

17. The method of claim 11, wherein the perfusion is measured quantitatively as cerebral blood volume (CBV).

18. The method of claim 11, wherein the patient remains on a patient support table of a C-arm X-ray device during the obtaining of the first CT-like data set and the second CT-like data set.

19. A computer program product, the product being stored or distributed on a non-transitory computer readable medium, the product comprising:
   instructions executable on a computer so as to configure the computer to:
      obtain a first computed tomographic (CT)-like data set and process the first CT-like data set so that a first voxel data set is produced;
      obtain a second CT-like data set where the patient has been administered an intravascular contrast agent and process the second CT-like data set so that a second voxel data set is produced;
      subtract the first voxel set from the second voxel set to produce a third voxel set, the third voxel data set including contrast enhanced vasculature;
      form a fourth voxel data set from the contrast-enhanced vasculature of the third voxel data set by segmenting the contrast-enhanced vasculature of the third voxel data set; and
      excise the fourth voxel data set from the third voxel data set to form a fifth voxel data set.

* * * * *